(12) United States Patent  
Scarberry et al.

(10) Patent No.: US 7,632,238 B1
(45) Date of Patent: Dec. 15, 2009

(54) ORAL MEASUREMENT DEVICE AND METHOD

(75) Inventors: Eugene N. Scarberry, Trafford, PA (US); Lance Busch, Trafford, PA (US); George Clinton Dungan, II, Chatswood (AU)

(73) Assignee: RIC Investments LLC, Wilmington, DE (US)

( * ) Notice: Subject to any disclaimer, the term of this patent is extended or adjusted under 35 U.S.C. 154(b) by 80 days.

(21) Appl. No.: 11/440,908

(22) Filed: May 25, 2006

Related U.S. Application Data

(60) Provisional application No. 60/686,865, filed on Jun. 2, 2005.

(51) Int. Cl.
*A61B 5/117* (2006.01)
*A61B 5/103* (2006.01)
(52) U.S. Cl. .................................................. 600/590
(58) Field of Classification Search ................. 600/587, 600/590; 433/56, 73, 29, 217.1, 97
See application file for complete search history.

(56) References Cited

U.S. PATENT DOCUMENTS

| | | | |
|---|---|---|---|
| 3,336,670 A * | 8/1967 | Heydenreich | ................. 433/56 |
| 4,226,025 A | 10/1980 | Wheeler | |
| 5,226,428 A | 7/1993 | Lee | |
| 5,361,506 A | 11/1994 | Beeuwkes, III | |
| 6,048,322 A | 4/2000 | Kushida | |
| 6,213,959 B1 | 4/2001 | Kushida | |
| 2008/0032253 A1* | 2/2008 | Montgomery et al. | .......... 433/29 |

FOREIGN PATENT DOCUMENTS

| JP | 10014913 A | * | 1/1998 |
|---|---|---|---|
| JP | 2003116819 A | * | 4/2003 |

* cited by examiner

*Primary Examiner*—Max Hindenburg
*Assistant Examiner*—Brian Szmal
(74) *Attorney, Agent, or Firm*—Michael W. Haas

(57) ABSTRACT

A device for taking measurements associated with an oral cavity of an individual. The device comprises a body and measuring indicia formed on the body which can be used to measure at least one parameter of the individual's mouth. An upper surface and a lower surface of the body are formed from an markable material capable of being marked by application of force from the individual's teeth. The body may also comprise a pallet measuring member constructed and arranged to extend operably from the body. The pallet measuring member has indicia formed thereon to enable measurement of the height of the individual's hard pallet. The body may also be provided with indicia to measure the length of the individual's tongue.

19 Claims, 4 Drawing Sheets

ORAL MEASUREMENT DEVICE AND METHOD

CROSS-REFERENCE TO RELATED APPLICATIONS

This application claims priority under 35 U.S.C. § 119(e) from provisional U.S. Patent Application No. 60/686,865 filed Jun. 2, 2005 the contents of which are incorporated herein by reference.

BACKGROUND OF THE INVENTION

1. Field of the Invention

The present invention relates to medical diagnostic devices.

2. Description of the Related Art

Sleep disordered breathing is a phenomenon that causes a patient to exhibit breathing pauses during sleep, resulting in excessive daytime sleepiness, sleep fragmentation, and intermittent hypoxia. Patients suffering from the disorder have a greater risk of developing diurnal hypertension, myocardial infarction, ventricular failure, pulmonary hypertension, cardiac dysrhythmias, and stroke. In addition to health problems, sleep disordered breathing significantly reduces the effectiveness and alertness of the individual during the day, which adversely effects the individual's lifestyle.

Sleep disordered breathing is typically diagnosed by polysomnographic testing. This procedure involves monitoring the patient overnight to record brain activity, eye movements, chin and leg muscle movements, cardiac rhythm, snoring intensity, oral-nasal airflow, respiratory muscle effort, and blood oxygen saturation. The test is time consuming, labor intensive, and expensive. Thus, it is desirable to pre-screen patients to determine whether they may be at risk for sleep disordered breathing in order to reduce the number of patients that are unnecessarily subjected to polysomnographic testing. In addition, earlier diagnosis and treatment of sleep disordered breathing would be promoted because the screening results would eliminate the reluctance of a physician to prescribe polysomnographic testing for those patients who do not exhibit dramatic symptoms.

Mathematical formulas have been developed to clinically predict whether a patient is likely to suffer from sleep disordered breathing. These mathematical models primarily rely on measurements of body mass index and neck circumference, two factors which are indicative of the obesity of the patient. Obesity is one of the important risk factors for sleep disordered breathing. However, not all patients who suffer from sleep disordered breathing are obese. Although prior mathematical models have combined the body mass index and neck circumference measurements with oxygen saturation levels, witnessed apneas, and questionnaire data, these mathematical models are of little use in screening patients who are not obese. A system of screening patients without relying on whether or not they are obese is desirable.

Another significant risk factor in the development of sleep disordered breathing is craniofacial dysmorphism (disproportionate craniofacial anatomy). Abnormalities associated with craniofacial dysmorphism include a reduction in the upper airway caliber, which makes the airway susceptible to collapse during sleep. Abnormalities in craniomandibular morphology, such as a narrow or posteriorly displaced mandible, are often found in patients that suffer from sleep disordered breathing. Another abnormality commonly found in these patients is a highly arched palate. Patients that suffer from sleep disordered breathing also commonly have a disproportionately large amount of oral soft tissue. This may include, for example, an oversized tongue and/or soft pallet. A system of quickly and accurately detecting the presence of a narrow or posteriorly displaced mandible, a highly arched palate, and/or a disproportionately large amount of oral soft tissue would facilitate the assessment of a patient's risk of suffering from sleep disordered breathing.

U.S. Pat. Nos. 6,048,322 and 6,213,959 to Kushida, the contents of which are incorporated herein by reference, disclose a tool for measuring an oral cavity of a patient, and a method of determining a predisposition of the patient to Obstructive Sleep Apnea Syndrome (OSA), which is one type of sleep disorder breathing, based on a mathematical model that implements the measurements taken with the tool as variables. The mathematical model also includes a body mass index (BMI) of the patient, and a measurement of the patient's neck circumference as variables. The tool disclosed by the Kushida patents measures a hard pallet height, a mandibular intermolar distance, a maxillary intermolar distance, and an overjet between the upper and lower incisors.

However, the tool and mathematical model described in the Kushida patents includes several drawbacks. For example, operation of the tool can be cumbersome, complicated, and uncomfortable for the patient being measured. Measurements taken with the tool must be taken separately, with the tool being repositioned for each measurement. In addition for several of the measurements, the tool must be positioned with a high level of precision in the patient's mouth to obtain accurate results. Consequently, the tool set forth in the Kushida patents may produce measurements that are not accurate. Further, the Kushida patents do not suggest including measurements and/or observations related to the amount of the patient's oral soft tissue in the determination of the patient's OSA risk.

SUMMARY OF THE INVENTION

The invention relates to a device for taking measurements associated with an oral cavity of an individual. In one aspect, the device comprises a body, and measuring indicia formed on the body. The indicia can be used to measure at least one parameter of the individual's mouth. The body comprises a markable material capable of being marked by application of force from the individual's teeth.

In another aspect, the body comprises an inner core on which the indicia are formed, and the markable material is formed as a cover over the core.

In another aspect, the body also comprises a pallet measuring member constructed and arranged to extend operably from the body. The pallet measuring member has indicia formed thereon to enable measurement of the height of the individual's hard pallet. The body may also be provided with indicia to measure the length of the individual's tongue. The present invention can be used as a diagnostic tool for sleep disordered breathing, or for any medical condition in which oral measurements can be used for diagnostics.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

BRIEF DESCRIPTION OF THE DRAWINGS

A specific embodiment of the invention is now described with reference to the accompanying drawings, wherein.

DETAILED DESCRIPTION OF THE PRESENTLY PREFERRED EMBODIMENTS OF THE INVENTION

Figure 1:
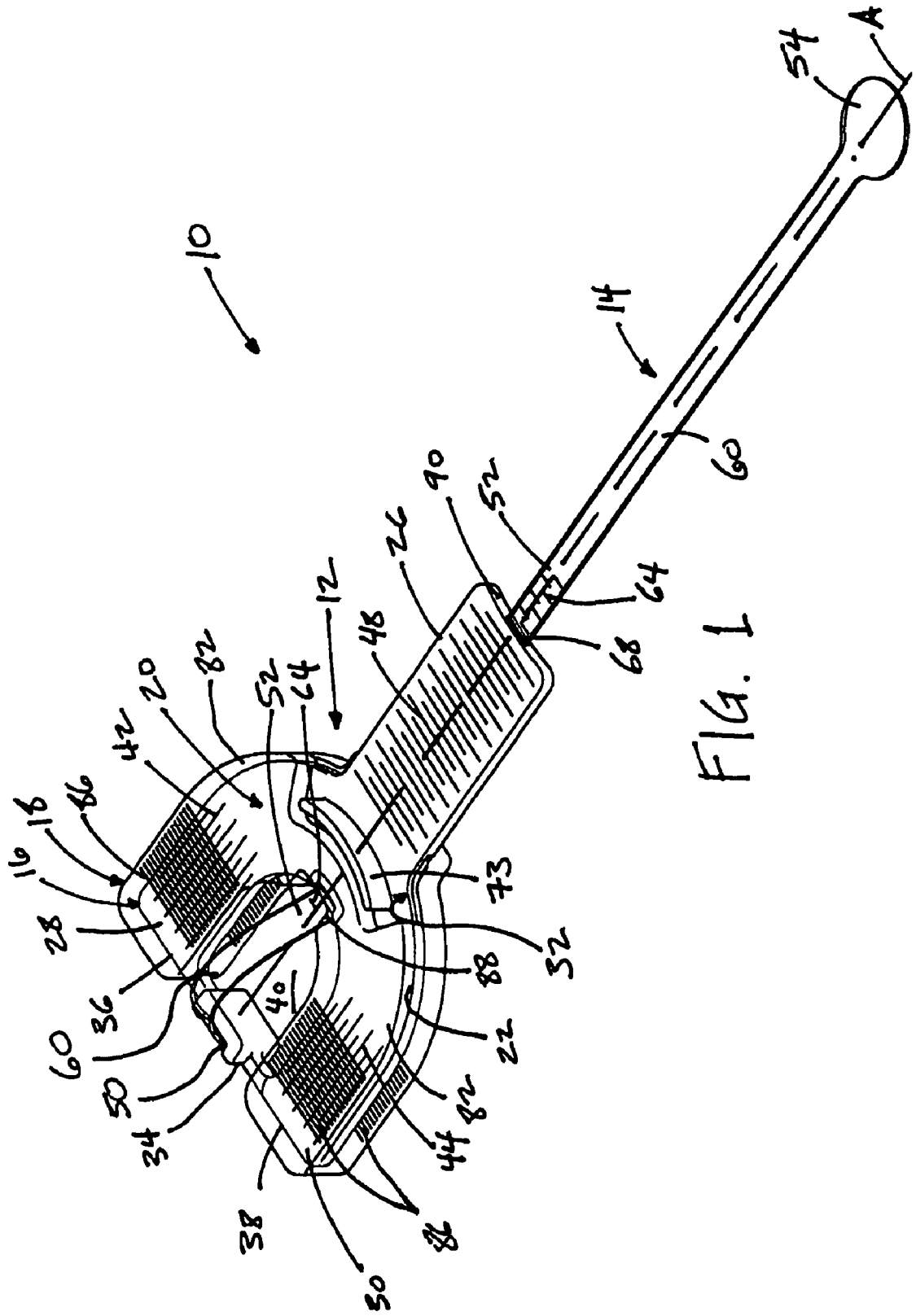
FIG. 1 is a top perspective view of a measurement device, according to one embodiment of the present invention.

FIG. 1 is a perspective view of an embodiment of a measurement device 10 in accordance with the present invention. Generally, device 10 is adapted for making several measurements associated with an oral cavity of an individual.

Figure 2:
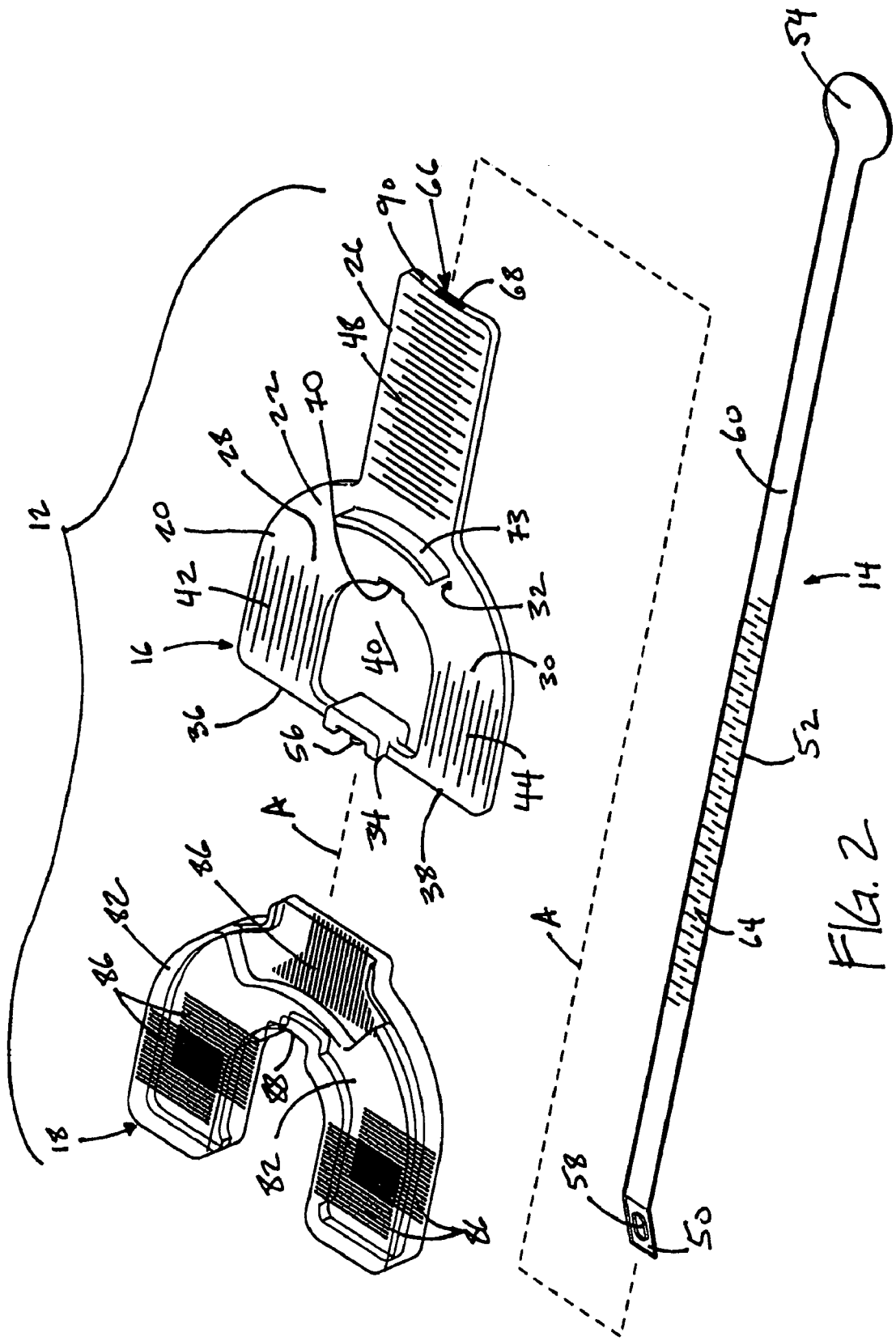
FIG. 2 is an exploded perspective view of the measurement device in accordance with an embodiment of the present invention.

The device 10, as shown in the perspective view of FIG. 1 and in the exploded view of FIG. 2, generally includes a body 12 and a pallet measuring member 14. Body 12 includes an inner core portion 16 and a cover portion 18. The cover portion 18 has a generally U-shaped configuration and generally surrounds a generally U-shaped portion 20 of core portion 16. In other words, U-shaped portion 20 of core portion 16 has a substantial portion thereof generally buried within the cover portion 18. The U-shaped portion 20 and the surrounding U-shaped cover portion 18 are generally sized and shaped to fit in a individual's mouth, and defines a shape that enables the individual's upper and lower teeth to engage therewith. In one embodiment, cover portion 18 is overmolded around U-shaped portion 20.

In one embodiment, inner core portion 16 is formed as a generally flat member, with a substantially planar upper surface 22 and a substantially planar lower surface 24. In addition to the aforementioned U-shaped portion 20, core portion 16 also includes an extension portion 26 formed integrally with the U-shaped portion 20. The U-shaped portion 20 includes a first, or left, side portion 28 and a second, or right, side portion 30 disposed in a generally parallel relation to each other. An arcuate portion 32 interconnects first side portion 28 with second side portion 30. Extension portion 26 extends outwardly from the arcuate portion 32. In addition, a support portion 34 interconnects distal ends 36 and 38 of the first side portion 28 and second side portion 30, respectively. A body opening 40 is surrounded (or defined) by first and second side portions 28, 30, support portion 34, and arcuate portion 32.

Figure 3:
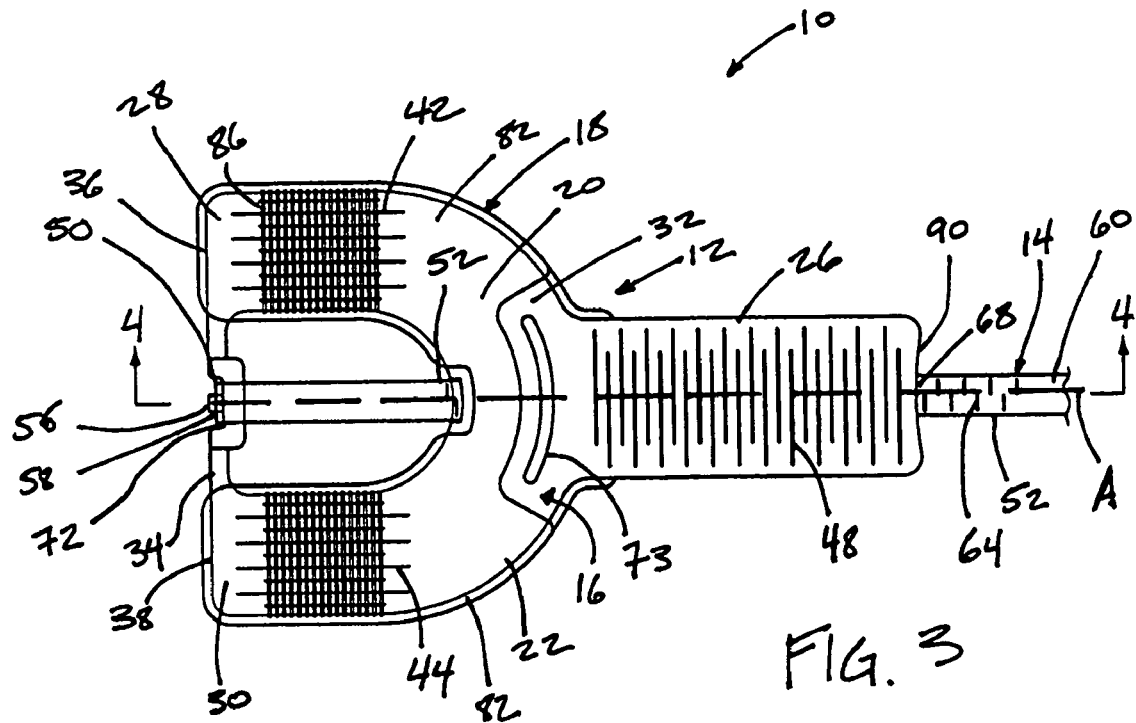
FIG. 3 is a top plan view of the measurement device, in accordance with an embodiment of the present invention.

As seen best in FIGS. 1-3, the upper surface 22 of inner core portion 16 is provided with measuring indicia. Such indicia may be in the form of lines, marks, numbers, letters, or any combination thereof. It will be appreciated that any visible marks or characters that enable measurements to be taken can be used. As shown, the first side portion 28 is provided with a first set of measuring indicia 42 that comprise a plurality of evenly spaced parallel lines. Such lines extend along first side portion 28 in a lengthwise direction (parallel to axis "A" in FIG. 1) of device 10. A second set of measuring indicia 44 are provided on upper surface 22 along the second side portion 30. The indicia 44 in the embodiment illustrated are disposed on second side portion 30 in a manner generally corresponding to the placement of measuring indicia 42 on first side portion 28. That is, the indicia 44 are shown as a plurality of evenly spaced parallel lines that run in a lengthwise direction relative to device 10. In a non-limiting example, measuring indicia 42, 44 may measure distances to positions on side portions 28, 30 from the central axis A of device 10.

Still referring to FIGS. 1-3, a third set of measuring indicia 48 are provided on the upper surface 22 of extension portion 26. Measuring indicia 48 include a set of demarcations that enable measurement along the length of extension portion 26. In the embodiment shown, the indicia 48 is in the form of a plurality of evenly spaced, parallel lines that run in a width direction of the device 10. That is, the lines forming indicia 48 run in a direction generally perpendicular to axis A and to the lines forming indicia 42, 44.

As seen best in FIG. 2, pallet measuring member 14 may be formed as a flat, thin, elongate structure. Pallet measuring member 14 includes a body attachment portion 50, a measurement portion 52, and a tabbed distal end portion 54. Pallet measuring member 14 is formed from a longitudinally-stiff, but orthogonally flexible plastic sheet. In one embodiment, the sheet material is transparent, but in other embodiments, an opaque material may be used.

Figure 5:
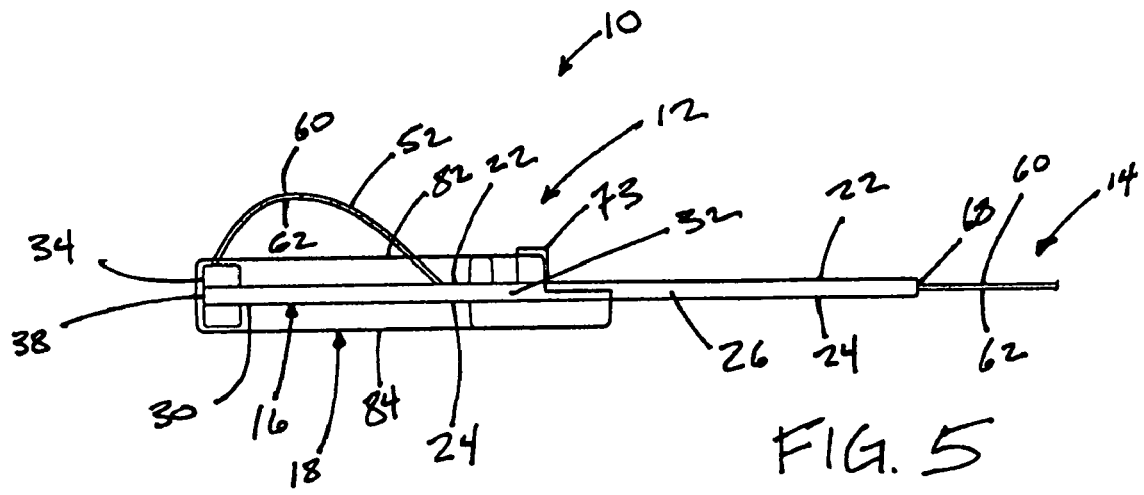
FIG. 5 is a side elevational view of the measurement device, according to one embodiment of the present invention.

The pallet measuring member 14 has an upper surface 60 and a lower surface 62 (See FIG. 5). The measurement portion 52 of pallet measuring member 14 has a fourth set of measuring indicia 64 provided on both the upper surface 60 and the lower surface 62. Measuring indicia 64 enables measurement along the length of measurement portion 52. Measuring indicia 64 may be in the form of spaced parallel lines that run in a width direction of device 10 (i.e., parallel to indicia 48 and perpendicular to axis A).

In the embodiment illustrated in FIGS. 1-3, body attachment portion 50 of pallet measuring member 14 is affixed to the support portion 34 of core portion 16 via a friction or snap-fit. Of course a variety of other adhesive or mechanical attachment mechanisms may be used without departing from the scope of the present invention including adhesives, latches, welds, etc. Specifically, as seen in FIG. 3, the support portion 34 has a projection 56, and the body attachment portion 50 has a complementary opening 58 for receiving projection 56 in a snap-fit relation. In other embodiments, body attachment portion 50 may be affixed to support portion 34 via one or more of a weld, an adhesive bond, a press fit, or other methods for affixing components to each other.

In the embodiment illustrated in FIGS. 1 and 2, end portion 54 is disposed at an end of measurement portion 52 opposite body attachment portion 50. End portion 54 includes a round tab formed at the end of measurement portion 52 that can be manually manipulated by the individual.

Figure 4:
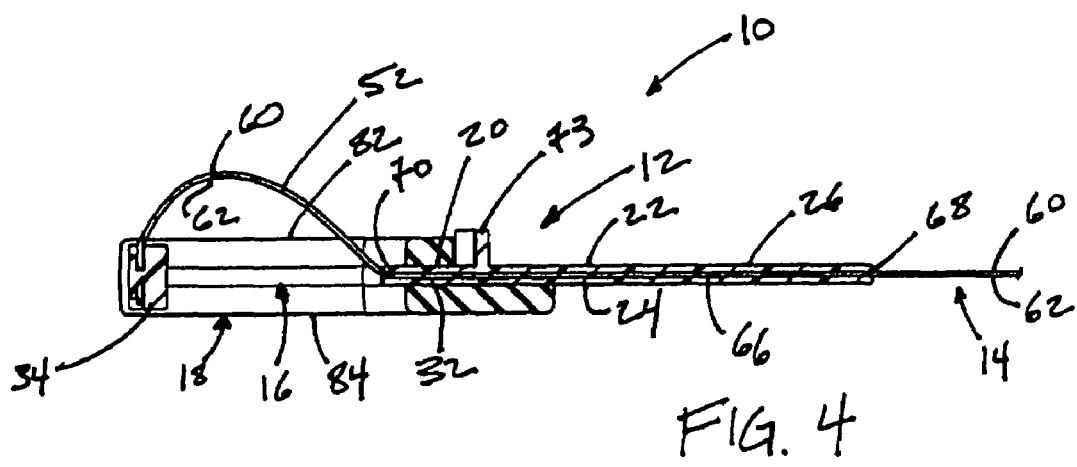
FIG. 4 is a cross-sectional view taken through the line 4-4 in FIG. 3.

As is shown best in the cross-sectional view of FIG. 4, pallet measuring member 14 extends through a conduit 66 formed through the core portion 16, along the central axis A of the device 10. Specifically, body attachment portion 50 may be introduced into conduit 66 at a first conduit opening 68 formed at an end of the extension portion 26 (See FIGS. 1 and 2). Pallet measuring member 14 is then threaded through conduit 66 and out a second conduit opening 70. After passing through conduit 66, body attachment portion 50 is then received at a mounting surface 72 of support portion 34 that carries projection 56 and that faces away from second conduit opening 70. In order for body attachment portion 50 to reach mounting surface 72, pallet measuring member 14 is passed over support portion 34 to mounting surface 72. Passing pallet measuring member 14 through conduit 66 and over support portion 34 to mounting surface 72 shapes measurement portion 52 in an arch. After the body attaching portion 50 is attached to surface 72 by pressing opening 58 over projection 56, further pushing the end portion 54 of pallet measuring member 14 into first conduit opening 68 will have the effect of raising the height of the apex of the arch formed by measurement portion 52 (See FIG. 3). Conversely, pulling the tab end 60 will have the effect of lowering the apex of the arch.

As may be seen in FIGS. 1-3, a ridge 73 is disposed on arcuate portion 32 at upper surface 22 of inner core portion 16. More specifically, ridge 73 protrudes out from arcuate portion 32 in a direction normal to upper surface 22, and extends an equal arclength in both directions from the central axis A of device 10. In the embodiments illustrated, ridge 73 is formed integral with arcuate portion 32. However, in other embodiments ridge 73 may be formed separately from, and be attached to, arcuate portion 32. Further, ridge 73 may, in some embodiments, not be curved along the arc of arcuate portion 32, and/or may simply be formed as a column, or a mechanical stop other than a ridge.

Figure 6:
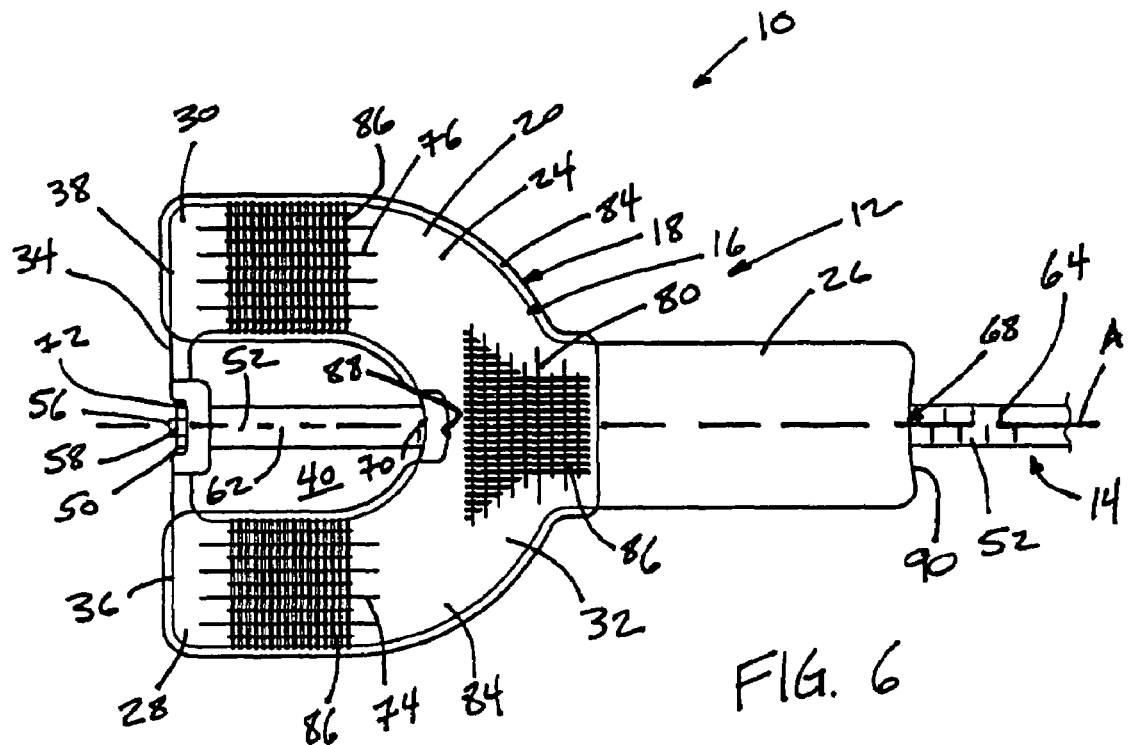
FIG. 6 is a bottom plan view of the measurement device, in accordance with one embodiment of the present invention.

FIG. 6, illustrates the underside and lower surface 24 of device 10. As shown, a fifth set of measuring indicia 74 is provided on first side portion 28 of inner core portion 16. In the embodiment illustrated here, measuring indicia 74 on lower surface 24 comprise evenly spaced, parallel lines that run in the same direction as measuring indicia 42 on upper surface 22, and demarcate a distance from the central axis A of device 10. As also shown, the lower surface 24 of second side portion 30 is provided with a sixth set of measuring indicia 76. In the embodiment shown, measuring indicia 76 on lower surface 24 comprise evenly spaced, parallel lines that run in the same direction as measuring indicia 44 on upper surface 22 of inner core portion 16 at second side portion 30, and demarcate a distance from the central axis A of device 10.

As also shown in FIG. 6, a seventh set of measuring indicia 80 is provided on arcuate portion 32 and on a portion of extension portion 26, at lower surface 24. Measuring indicia 80 are illustrated as including evenly spaced, parallel lines running perpendicular to the central axis A of device 10. However, in other embodiments, measuring indicia 80 may include lines, or other markings, that follow the arc of arcuate portion 32. Measuring indicia 80 are disposed on lower surface 24 in a region that corresponds to the position of ridge 73 on upper surface 22.

Each of the measuring indicia described herein may be provided in many different ways. For example, the indicia as described herein may be printed, painted, etched, molded, stamped, embossed, carved, or otherwise formed.

In the embodiment illustrated, inner core portion 16 is depicted as a single, integral member. The composition of inner core portion 16, as shown, may include a rigid, durable material, such as a rigid plastic like polycarbonate, or other materials. In one embodiment, the core portion 16 is formed of an opaque material with a high level of contrast with the indicia. In one embodiment, the core portion 16 is molded from a white material, and the indicia are formed from black paint or ink. It will be appreciated that although inner core portion 16 is represented in FIGS. 1-6 as a single member, in other embodiments some or all of side portions 28, 30, support portion 34, arcuate portion 32, and extension portion 26 may be formed as separate members and attached together via a conventional method such as, for example, welding, adhesive bonding, a snap-fit, a press fit, or other methods for attaching separate members.

Referring back to FIGS. 1 and 2, the cover portion 18 is in one embodiment formed from a clear or transparent material, enabling measuring indicia 42, 44, 48, 74, 76, 80 to be seen therethrough. However, in alternative embodiments, measuring indicia 42, 44, 48, 74, 76, 80 may be provided on cover portion 18 itself, and cover portion 18 may be formed of an opaque material. In such embodiments, the inner core portion 16 and cover portion 18 may be formed from the same material in a "one-shot" injection molding process, so that the body 12 is a one-piece, integrally molded structure, effectively eliminating the cover portion/core portion distinction.

Referring back to the illustrated embodiment, cover portion 18 provides an upper markable surface 82 above upper surface 22 of inner core portion 16, and a lower markable surface 84 below lower surface 24 of inner core portion 16. In one embodiment, markable surfaces 82, 84 are composed of a markable material capable of being marked by an application of force thereto. Specifically, in one embodiment, application of a biting force will leave an impression (i.e., indentation), marking the location of the individual's teeth. In one embodiment, cover portion 18 is composed of a clear thermal plastic material which softens when heated above ambient temperature such as ethylene vinyl acetate (EVA). However, one skilled in the art can best appreciate that a variety of other thermal plastic materials may be utilized without departing from the spirit or scope of the present invention.

To improve visibility of the boundaries of indentations in the clear surfaces provided by the EVA, texturing 86 may be formed on markable surfaces 82, 84 of the clear EVA above measuring indicia 42, 44, 48, 74, 76, 80. The texturing 86 may enhance the viewing of markings left in cover portion 18. More particularly, in embodiments that implement a clear cover, the texturing 86 enhances perception of the precise positions of indentations left in the clear surfaces of the cover portion 18.

In other instances, markable surfaces 82, 84 may be formed from a wax, or other material including electrical or chemical indicating devices that are capable of indicating the location where force is applied. Although cover portion 18 is shown as a single component, it will be appreciated that, for example, markable surfaces 82, 84 may be provided by separate components. In previously described embodiments wherein body 12 is provided as a single integral component, the single component may provide the functional attributes of both inner core portion 16 (e.g., side portions 28, 30, support portion 34, arcuate portion 32, extension portion 26, and ridge 73) and cover portion 18 (e.g., upper markable surface 82 and lower markable surface 84).

Referring to FIG. 3, upper markable surface 82 is illustrated as covering upper surface 22 of inner core portion 16 at side portions 28, 30. Upper markable surface 82 is provided over part of upper surface 22 at arcuate portion 32, but does not extend to the region of upper surface 22 at arcuate portion 32 at which ridge 73 is formed. FIGS. 2 and 3 also illustrate that a cover conduit opening 88 is disposed to coincide with conduit opening 70 such that pallet measuring member 14 may pass therethrough.

Turning to FIG. 6, lower markable surface 84 is shown covering lower surface 24 of inner core portion 16 at side portions 28, 30, arcuate portion 32, and a portion of extension portion 26. More particularly, lower markable surface 84 extends along extension portion 26 away from arcuate portion 32 far enough to cover measuring indicia 80 provided on extension portion 26.

In another embodiment, the marking formed on the body upon application of a biting force need not be formed on the exterior surfaces of the cover portion 18. Rather, forces may be transmitted to the core portion 16 so as to be visible on the core portion 16, or inner surfaces of the cover portion 18. This may be accomplished with use of a combination of markable materials and suitable chemical components, such as the manner in which carbon copies are made.

In use, an individual heats device 10 with hot water (or other heating agent). The individual may heat device 10 with hot water by placing device 10 in the water such that cover portion 18 is submerged. In one embodiment, water at boiling temperature is used. This will soften the EVA of cover portion 18 to receive an impression of the individual's teeth. Once cover portion 18 has been heated to the appropriate temperature, device 10 is removed from the water and U-shaped portion 20 of body 12 is inserted into the individual's mouth. Device 10 is positioned within the individual's mouth such that the front surface of the individual's upper incisors abut ridge 73, which acts as a guide, ensuring that device 10 is positioned appropriately within the individual's mouth.

Once device 10 has been positioned correctly in the individual's mouth, the individual bites down so that the individual's teeth engage cover portion 18, which is still soft from having been heated, creating an impression of the individual's teeth in cover portion 18. More particularly, referring to FIGS. 3 and 6, the impression of the individual's teeth will include an impression of the individual's left and right upper molars formed in upper markable surface 82 above measuring indicia 42, 44, respectively. In addition, impressions of the individual's left and right lower molars formed in lower markable surface 84 over measuring indicia 74, 76, respectively. Furthermore, impressions of the individual's lower incisors and cuspids are formed in lower markable surface 84 over measuring indicia 80 of arcuate portion 32 and/or extension portion 26.

While the individual's teeth are engaged with cover portion 18, pallet measuring member 14 is fed through conduit 66 from first conduit opening 68 to second conduit opening 70 to increase the height of the apex of the arch (illustrated best in FIG. 4) formed by measurement portion 52 of pallet measuring member 14. The height of the apex of the arch is increased until measurement portion 52 contacts the hard pallet of the individual. In one embodiment, the pallet height can be measured prior to the device being removed from the individual's mouth. For example, a physician may view the indicia 64 at first conduit opening 68 to determine how much of the measurement portion 52 has been fed through conduit opening 68. Thus, the pallet height may be measured while the device 10 is still in the individual's mouth. Alternatively, the pallet measuring member 14 may be manually held fixed relative to body 12 after the arch has reached (contacted) the individual's pallet, and the individual or physician can retain this fixed relation as the device 10 is taken out of the individual's mouth. In this methodology, a pallet height reading may be taken at either the opening 68 or at opening 70, as non-limiting examples. In another embodiment, a mechanism, such as a pin extending through extension portion 26 may be used to fix, or pin, the pallet measuring member 14 to the body 12 after the arch has reached the pallet. This would enable the individual or physician to measure the pallet height after the device 10 is removed from the individual's mouth, and without the need to manually maintain the pallet measuring member 14 in fixed relation to body 12.

It will be appreciated that in other embodiments of the invention, alternate methods of adjusting the height of pallet measuring member 14 may be employed. For example, pallet measuring member 14 may be deployed from body 12 via a reel assembly, rather than being fed through conduit 66, to increase the height of the apex of the arch. In other embodiments, a pallet measuring member may be implemented that does not form an arch, but simply extends upward from body 12 to measure the location of the individual's hard pallet. For instance, the pallet measuring member may telescopically extend from the body. Alternatively, pallet measuring member 14 may include a member pivotally carried on body 12 that pivots up to contact the hard pallet. One skilled in the art can appreciate that a variety of other mechanisms for measuring the individual's hard pallet may be implemented in device 10 without departing from the scope of the invention. For example, body 12 may carry an electronic device that determines the position of the hard pallet through the emission and detection of sonic, ultrasonic, and/or electromagnetic radiation within the oral cavity of the individual. This may employ reflective technology that is used in various commonly available distance measuring devices.

Once device 10 has been removed from the mouth of the individual, the maxillary intermolar distance, the mandibular intermolar distance, and the overjet or overlap between the upper and lower incisors is determined from the data recorded by the upper and lower impressions created on markable surfaces 82, 84.

Referring to FIG. 3, the maxillary intermolar distance is determined from the upper impression of the individual's upper molars formed in upper markable surface 82. More specifically, using the locations of the impressions of the individual's upper second molars, the spacing between the mesial surfaces of the crowns of these molars is determined based on measuring indicia 42, 44 at side portions 28, 30.

Turning to FIG. 6, the mandibular intermolar distance, and the overjet or overlap between the upper and lower incisors are determined from the lower impression of the individual's lower molars and lower incisors formed in lower markable surface 84. With respect to the mandibular intermolar distance, the impressions of the individual's lower molars and measuring indicia 74, 76 are used in a manner that corresponds to the determination of maxillary intermolar distance described above to ascertain the distance between the mesial surfaces of the crowns of the lower second molars. The impressions of the individual's lower incisors are formed in the region of measuring indicia 80. Using measuring indicia 80, the offset of the impressions of the lower incisors and the position of the upper incisors when the front surface of the upper incisors were engaged with ridge 73 can be established.

Referring to FIGS. 1 and 3, before device 10 is inserted into the individual's mouth, or after device 10 has been removed from the individual's mouth, the individual can use device 10 to measure the length of the individual's tongue. More specifically, the individual positions the device 10 so that a concave end surface 90 formed at the distal edge of extension portion 26 engages the front surface of the individual's upper incisors, and the individual extends the tongue along extension portion 26 toward arcuate portion 32. Measuring indicia 48 enable the physician to determine the length of the tongue from the incisors to the tip of the extended tongue. Alternatively, the individual may execute the measurement via observation of the extension of the tongue in a reflective surface (e.g., a mirror), or by marking the extension of the tongue along extension portion 26 with a finger, and then removing extension portion 26 from the individual's mouth and observing the marked position.

In the embodiments illustrated, device 10 is intended as a disposable unit to be used by a single individual and then discarded. However, such examples are not limiting, and other embodiments in which some or all of inner core portion 16, pallet measuring member 14, and cover portion 18 are reusable may be implemented. For example, inner core portion 16 may be a reusable component, and disposable covers and/or pallet measuring members may be attached thereto for use with each of a plurality of individuals.

Some or all of the measurements obtained by the individual via device 10 may be utilized in determining the individual's predisposition to sleep disordered breathing. For example, the palatial height, the maxillary intermolar distance, the mandibular intermolar distance, and the incisor ovejet, along with the individual's neck circumference and Body Mass Index (BMI), may be used in the method disclosed in U.S. Pat. Nos. 6,048,322 and 6,213,959 to Kushida, or other mathematical models, in order to determine a morphometric model value (MMV) for the individual that is predictive of the individual's predisposition to OSA.

In other embodiments, the measurement of the oral cavity including the palatial height of the hard pallet, the maxillary intermolar distance, the mandibular intermolar distance, and the incisor ovejet, taken using device 10, may be used in conjunction with one or more soft tissue measurements to ascertain the individual's predisposition to sleep disordered breathing. In a non-limiting example, the soft tissue measurements may include the length of the tongue, taken using device 10, a width of the tongue, and a size of the opening formed by the top of the tongue and the soft pallet at the back of the oral cavity. In some instances, the width of the tongue may be determined by the observation of "scalloping," or permanent impressions made by the lower teeth, on the sides of the individual's tongue. The size of the opening formed by the top of the tongue and the soft pallet may be determined through simple observation.

It should be appreciated that when referring to a "physician" herein, this can also refer to any third person that is trained in taking measurements with device 10.

It should be appreciated that the device of the present invention can be used to take oral measurements for any diagnostic purpose, not just for sleep disorder breathing problems.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims.

What is claimed is:

1. A device for taking measurements associated with an oral cavity of an individual, comprising:
a body, wherein at least a portion of the body has a U-shaped portion for insertion into the oral cavity of an individual, the U-shaped portion having a first side portion and a second side portion, the first side portion and the second side portion being disposed in a parallel relation to one another, and an arcuate portion interconnecting the first side portion with the second side portion;
measuring indicia formed on either or both of the first side portion and the second side portion of the U-shaped portion of the body which can be used to measure at least one parameter of an individual's mouth;
the first side portion and the second side portion of the U-shaped portion of the body comprising a markable material capable of being marked by application of force from an individual's teeth.

2. The device of claim 1, wherein the indicia comprises right side indicia which can be used to measure at least one parameter of the individual's teeth on the right side of the individual's mouth, and left side indicia with can be used to measure at least one parameter of the individual's teeth on the left side of the individual's mouth.

3. The device of claim 1, wherein the indicia comprises upper indicia which can be used to measure at least one parameter of the individual's upper teeth.

4. The device of claim 3, wherein the at least one parameter of the individual's upper teeth includes a maxillary intermolar distance.

5. The device of claim 1, wherein the indicia comprises lower indicia which can be used to measure at least one parameter of the individual's lower teeth.

6. The device of claim 5, wherein the at least one parameter of the individual's lower teeth includes a mandibular intermolar distance.

7. The device of claim 1, wherein the at least one parameter of the individual's mouth includes an ovejet between the individual's upper and lower incisors.

8. The device of claim 1, further comprising a pallet measuring member constructed and arranged to slidably extend out from and retract into the body, the pallet measuring member having indicia formed thereon to enable measurement of the height of the individual's hard pallet.

9. The device of claim 8, wherein the pallet measuring member is slidably extended into the individual's mouth from the body until the pallet measuring member contacts the individual's hard pallet.

10. A device for taking measurements associated with an oral cavity of an individual, comprising:
a body;
visible measuring indicia in the form of lines, marks, numbers, letters, or any combination thereof, formed on the body which can be used to measure at least one parameter of the individual's mouth;
the body comprising a markable material capable of being marked by application of force from the individual's teeth, wherein the body comprises an inner core portion on which the visible measuring indicia are formed, and a cover portion separate from and covering the inner core portion and the visible measuring indicia on which the markable material is provided.

11. The device of claim 10, wherein the cover portion is transparent to enable the indicia to be viewed therethrough.

12. A device for taking measurements associated with an oral cavity of an individual, comprising:
a body;
measuring indicia formed on the body which can be used to measure at least one parameter of the individual's mouth;
the body comprising a markable material capable of being marked by application of force from the individual's teeth; and
a pallet measuring member constructed and arranged to extend operably from the body, the pallet measuring member having indicia formed thereon to enable measurement of the height of the individual's hard pallet, wherein the pallet measuring member is structured to be extended into the individual's mouth via the body with a height of an apex of an arc formed by the pallet measuring member increasing until the pallet measuring member contacts the individual's hard pallet.

13. A device for taking measurements associated with an oral cavity of an individual, comprising:

a body;

measuring indicia formed on the body which can be used to measure at least one parameter of the individual's mouth;

the body comprising a markable material capable of being marked by application of force from the individual's teeth; and a pallet measuring member constructed and arranged to extend operably from the body, the pallet measuring member having indicia formed thereon to enable measurement of the height of the individual's hard pallet, wherein the pallet measuring member is fed into the individual's mouth via the body until the pallet measuring member contacts the individual's hard pallet, wherein the pallet measuring member is fed into the individual's mouth via a conduit formed in the body.

14. A device for taking measurements associated with an oral cavity of an individual, comprising:

a body;

measuring indicia formed on the body which can be used to measure at least one parameter of the individual's mouth;

the body comprising a markable material capable of being marked by application of force from the individual's teeth; and an extension from the body, wherein the indicia formed on the body comprise indicia formed on the extension that enable measurement of a length of the individual's tongue.

15. The device of claim 14, wherein the extension is formed such that the individual's tongue can be extended along the extension to enable measurement thereof.

16. The device of claim 15, wherein the extension forms a concave end surface that functions as a locator for positioning the extension with respect to the individual's mouth so that the length of the individual's tongue can be measured accurately.

17. The device of claim 16, wherein the extension is positioned for measuring the length of the individual's tongue such that the individual's upper incisors engage the concave end surface.

18. A device for measuring oral parameters of a individual, comprising:

a body;

measuring indicia formed on the body and arranged to be used to measure a maxillary intermolar distance, a mandibular intermolar distance, and an incisor overjet of the individual, wherein the body comprises a markable material capable of being marked by the individual's teeth at positions corresponding to the measuring indicia to enable measurements of the maxillary intermolar distance, the mandibular intermolar distance, and the incisor overjet of the individual; and a pallet measuring member carried by the body and constructed to measure a height of the hard pallet of the individual.

19. A device according to claim 18, wherein the pallet measuring member comprises indicia formed on an archable member that can be moved relative to the body until the archable member forms an arch that reaches the individual's hard pallet.

* * * * *